(12) United States Patent
Yagi et al.

(10) Patent No.: US 9,063,106 B2
(45) Date of Patent: Jun. 23, 2015

(54) AUTOMATIC ANALYZER AND METHOD FOR USING THE SAME

(75) Inventors: Kenichi Yagi, Mito (JP); Yoshimitsu Takagi, Hitachinaka (JP); Hitoshi Ohtake, Hitachinaka (JP)

(73) Assignee: HITACHI HIGH-TECHNOLOGIES, CORPORATION, Tokyo (JP)

( * ) Notice: Subject to any disclaimer, the term of this patent is extended or adjusted under 35 U.S.C. 154(b) by 1137 days.

(21) Appl. No.: 12/181,868

(22) Filed: Jul. 29, 2008

(65) Prior Publication Data

US 2009/0035867 A1 Feb. 5, 2009

(30) Foreign Application Priority Data

Jul. 31, 2007 (JP) ................. 2007-199326

(51) Int. Cl.
- *G01N 35/02* (2006.01)
- *G01N 35/00* (2006.01)
- *G01N 21/00* (2006.01)
- *G01N 35/10* (2006.01)

(52) U.S. Cl.
CPC ........... *G01N 35/1002* (2013.01); *Y10T 436/11* (2015.01); *Y10T 436/115831* (2015.01); *G01N 2035/00673* (2013.01)

(58) Field of Classification Search
CPC ................ G01N 2035/00673; G01N 35/1002; G01N 35/00603; G01N 35/00663; G01N 35/00732; G01N 35/0092; G01N 35/025; G01N 2035/0415; G01N 35/04
USPC ......................... 436/50, 43; 422/67
See application file for complete search history.

(56) References Cited

U.S. PATENT DOCUMENTS

| 3,784,826 | A | * | 1/1974 | Bagshawe et al. ............ 250/328 |
| 5,389,339 | A | * | 2/1995 | Petschek et al. ................ 422/64 |
| 6,080,364 | A | * | 6/2000 | Mimura et al. ................. 422/67 |
| 7,749,441 | B2 | | 7/2010 | Hanawa et al. |
| 2005/0207938 | A1 | * | 9/2005 | Hanawa et al. .................. 422/64 |
| 2006/0002820 | A1 | * | 1/2006 | Baumann et al. ............ 422/68.1 |
| 2006/0004530 | A1 | | 1/2006 | Miyamoto et al. |
| 2007/0038491 | A1 | * | 2/2007 | Samuhel et al. .................. 705/8 |
| 2008/0063570 | A1 | * | 3/2008 | Fujino et al. .................... 422/99 |
| 2009/0305392 | A1 | * | 12/2009 | Alfredsson et al. ........ 435/286.1 |

FOREIGN PATENT DOCUMENTS

| CN | 1576849 A | 2/2005 |
| JP | 4-43962 A | 2/1992 |
| JP | 4-50654 A | 2/1992 |
| JP | 11-304807 A | 11/1999 |
| JP | 2000-321283 | 11/2000 |
| JP | 2005-037171 | 2/2005 |
| JP | 2005-121492 A | 5/2005 |

* cited by examiner

Primary Examiner — Dean Kwak
(74) Attorney, Agent, or Firm — Mattingly & Malur, PC (57) ABSTRACT

A method for an automatic analyzer to reduce a user's workload required when a reagent is placed therein, and thereby facilitating change of the operation mode of the automatic analyzer. The automatic analyzer including a first reagent storing unit that is capable of storing a plurality of reagent cassettes and a second reagent storing unit that is capable of storing a plurality of reagent cassettes. When the first reagent storing unit does not have empty space for a required reagent, and all reagents required for analysis operation for a selected operation set cannot be completely transferred to the first reagent storing unit, keeping the required reagent waiting in the second reagent storing unit. Further, when the first reagent storing unit is provided with empty space, the required reagent is transferred to the first reagent storing unit.

5 Claims, 6 Drawing Sheets

CONFIRMATION

THE FOLLOWING REAGENTS ARE INSUFFICIENT

| ANALYSIS ITEM NAME | (A) THE SCHEDULED NUMBER OF ANALYSES | (B) THE NUMBER OF ANALYSES THAT CAN BE MADE | (C) THE INSUFFICIENT NUMBER OF TESTS | (D) THE NUMBER OF NEW REAGENTS |
|---|---|---|---|---|
| ALB | 200 | 100 | 100 | 1 |
| AST | 500 | 100 | 400 | 2 |
| BUN | 250 | 80 | 170 | 1 |
| CRE | 200 | 80 | 120 | 1 |
| | | | | |
| | | | | |

AUTOMATIC ANALYZER AND METHOD FOR USING THE SAME

BACKGROUND OF THE INVENTION

1. Field of the Invention

The present invention relates to an automatic analyzer for performing qualitative/quantitative analysis of a living body sample such as blood and urine and a method for using the automatic analyzer. The invention also relates to a computer program and a recording medium to which the program is written.

2. Description of the Related Art

In the field of automatic analysis, one analyzer may be used in various operation modes. For example, a limited number of items sometimes require multi-sample analysis at the time of a blood test in periodic medical examination. That is because the blood test does not require analyses covering many items. In such a case, reagents sufficient for the analysis of each item are placed in an analyzer so as to avoid the shortage of reagents during the multi-sample analysis that takes a long time to complete. In contrast to this, when the analyzer copes with requests for analyses covering all items (for example, operation at night), the number of requested samples is small, and accordingly, it is not necessary to analyze many samples. However, multi-item analysis is required. In such a case, it is necessary to place many kinds of reagents in the analyzer so that many analysis items can be handled.

As described above, how to place reagents differs depending on an operation mode. For this reason, if one analyzer is configured to have two or more operation modes, it is necessary to determine analysis items, and the number of tests, required for each of the operation modes, and to replace a reagent with a required one. Also for this purpose, reagent replacement work should be made simple and easy.

Recently, with the increase in analysis speed, the number of reagents consumed by an analyzer per hour tends to increase. As one of methods for enabling long-time analysis by the analyzer, the number of reagents which can be stored in a reagent storing unit of the analyzer is sometimes increased.

Accordingly, to change an operation mode which requires a user to place reagents associated with the operation mode, the user checks kinds of currently placed reagents, and the number of tests which can be made with the currently placed reagents on a screen, or the like. The user then removes an unnecessary reagent from the reagent storing unit, and places a necessary reagent in the reagent storing unit. In the case of this method, with increase in the number of reagents placed in the reagent storing unit, human errors more easily occur. For example, when the user places a reagent, there is a higher possibility that the user will place the reagent in the wrong place or the user will remove a necessary reagent. In contrast to normal addition of a reagent, for example, when an operation mode is changed to another operation mode that requires transfer of many reagents from a refrigerator for storing reagents to the reagent storing unit of the analyzer, reagent placement work becomes more complicated. As a result, an excessive load is put on the user.

JP-A-2000-321283 discloses a configuration in which the workability of reagent replacement by a user is improved by moving a reagent bottle, which falls short of a reagent, to a position at which the reagent bottle is taken out.

JP-A-2005-37171 discloses an automatic analyzer in which a sample and a reagent are dispensed into each of a plurality of vessels so that the sample and the reagent react with each other, and in which a liquid generated by the reaction is measured. The automatic analyzer includes: first reagent storing means for storing a reagent used for the reaction; second reagent storing means for supplementarily storing a reagent; and reagent transfer means for transferring a reagent from the second reagent storing means to the first reagent storing means. According to JP-A-2005-37171, the automatic analyzer makes it possible to reduce a load put on an operator, and to minimize the number of times analysis is interrupted because a shortage of reagents during the analysis does not occur.

SUMMARY OF THE INVENTION

An object of the present invention is to provide an automatic analyzer that is capable of reducing a user's workload required when a reagent is placed, and thereby facilitating change of the operation mode of the automatic analyzer.

According to one aspect of the present invention, there is provided an automatic analyzer comprising:
  a reaction unit including a plurality of vessels;
  a first reagent storing unit that is capable of storing a plurality of reagent cassettes;
  a sample dispenser for dispensing a sample into the reaction unit;
  a reagent dispenser for dispensing a reagent corresponding to an analysis item from the first reagent storing unit into the reaction unit;
  a second reagent storing unit that is capable of storing a plurality of reagent cassettes; and
  reagent cassette transfer means that is capable of transferring a reagent between the first reagent storing unit and the second reagent storing unit,
  the automatic analyzer further comprising reagent selection means for selecting a reagent to be used for analysis operation based an operation set, wherein the operation set specifies a combination of an analysis item and the scheduled number of analyses corresponding to the analysis item.

According to the present invention, placement of reagents can be automatically changed. This makes it possible to reduce a load put on a user, which is caused by a change of the operation mode of an automatic analyzer.

Furthermore, according to the present invention, the change and preparation of reagents suitable for an operation mode can be facilitated.

DESCRIPTION OF THE PREFERRED EMBODIMENTS

Embodiments of the present invention will now be described with reference to the accompanying drawings.

Figure 1:
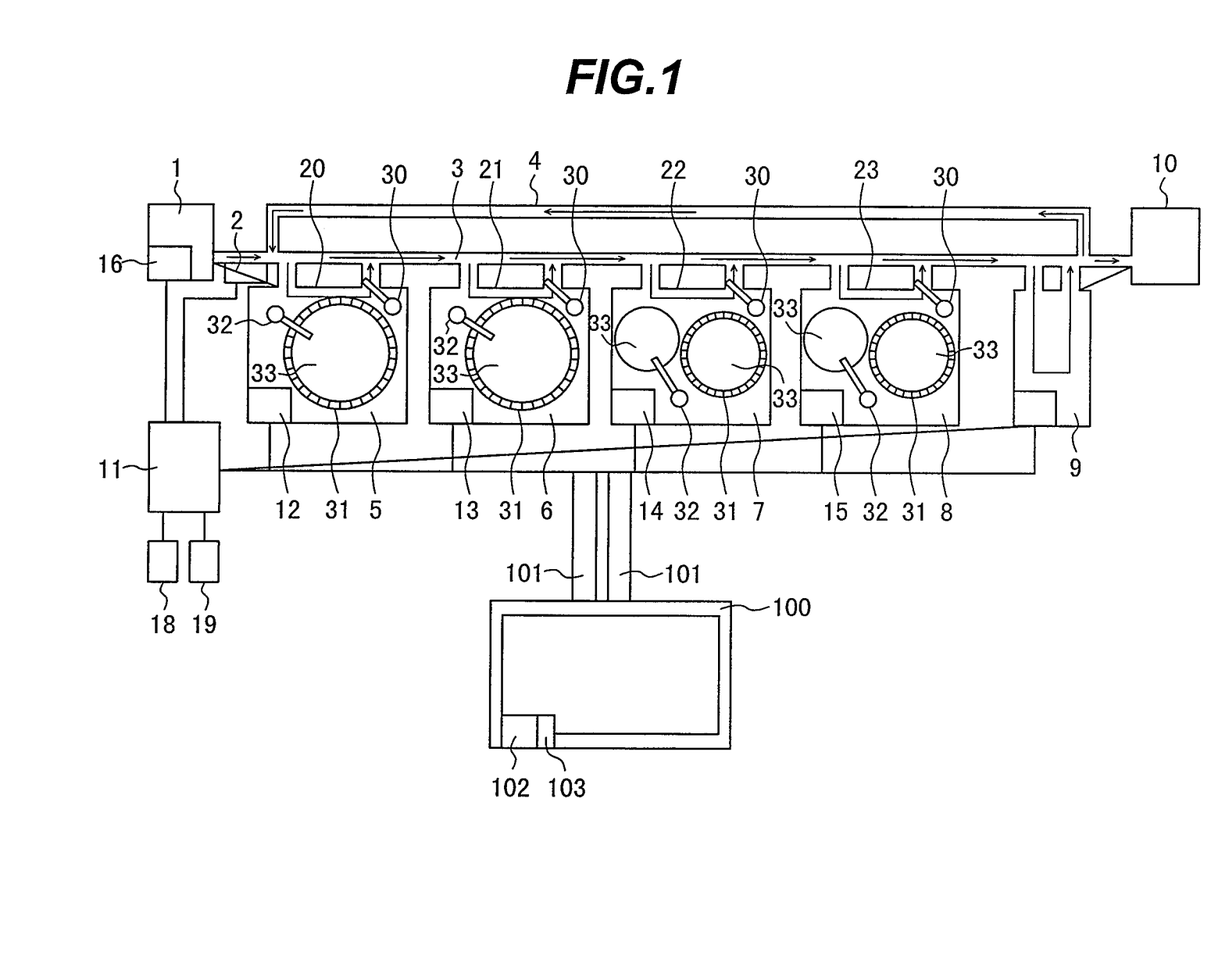
FIG. 1 is a diagram schematically illustrating a configuration of an automatic analyzer according to one embodiment of the present invention.

FIG. 1 is a diagram schematically illustrating the configuration of an automatic analyzer according to one embodiment of the present invention.

The automatic analyzer according to this embodiment includes a sample rack loading unit 1, an ID reading unit 2, a transfer line 3, a reexamination transfer line 4, analysis modules 5, 6, 7, and 8, a sample rack standby section 9, a sample rack collecting unit 10, a second reagent storing unit 100, and an overall control computer 11. The analysis modules 5, 6, 7, and 8 and the sample rack loading unit 1 are equipped with control computers 12, 13, 14, 15, and 16, respectively. In addition, the overall control computer 11 is equipped with an operation unit 18 and a display unit 19.

The sample rack loading unit 1 is a unit used to load a plurality of sample racks, each of which holds one or more samples (specimens). The analysis modules 5, 6, 7, and 8 are units which are capable of separately performing automatic analysis; they are located along and detachably connected to the transfer line 3. The transfer line 3 leads to the analysis modules 5, 6, 7, and 8 through lead-in lines 20, 21, 22, and 23, respectively, so that a sample (specimen) can be transferred therebetween. The number of the analysis modules may be arbitrarily determined; in this embodiment, that number is four. Further, in this embodiment, all of the analysis modules are biochemical analysis modules. The analysis modules may also include a combination of a biochemical analysis module and another analysis module (for example, an electrolyte analysis module).

Each of the analysis modules 5, 6, 7, and 8 is provided with a sample dispenser 30 for dispensing a sample (specimen) that has been transferred to the analysis module with the sample placed in a sample rack; and a reaction vessel 31 in which the sample (specimen) is made to react. In addition, each of the analysis modules 5, 6, 7, and 8 is further provided with a reagent dispenser 32 for dispensing a reagent into the reaction vessel 31 into which the sample has been dispensed; and a first reagent storing unit 33 that holds a reagent cassette filled with a reagent to be dispensed into the reaction vessel 31. In this embodiment, each of the analysis modules 5 and 6 is provided with one first reagent storing unit 33; each of the analysis modules 7 and 8 is provided with two first reagent storing units 33. As above, the analysis modules can each have a single or multiple first reagent storing units 33.

The second reagent storing unit 100 is connected via a reagent transfer line 101 to the first reagent storing units 33 included in the analysis modules 5, 6, 7, and 8. However, one analysis system need not have only one second reagent storing unit 100 as above; instead, each analysis module within the analysis system can have one second reagent storing unit 100. Alternatively, one second reagent storing unit 100 can be provided for analysis modules of the same kind such as biochemical analysis modules or electrolyte analysis modules.

The second reagent storing unit 100 includes a reagent supply unit 102 to which a user supplies reagents; and a reagent identification unit 103 for identifying the kinds of the supplied reagents.

Moreover, the second reagent storing unit 100 may also have the function of refrigerating the reagents so as to store them for a long period of time.

TABLE 1

| Example of operation set | |
|---|---|
| Item | Analysis samples |
| Operation Set 1 (for periodic medical examination) | |
| AST | 600 |
| ALT | 600 |
| TP | 600 |
| ALP | 600 |
| IP | 600 |
| UA | 600 |
| GLU | 600 |
| Ca | 600 |
| Mg | 600 |
| ChE | 600 |
| Operation Set 2 (for nighttime) | |
| AST | 100 |
| ALT | 100 |
| TP | 100 |
| ALP | 100 |
| IP | 100 |
| UA | 100 |
| GLU | 100 |
| Ca | 100 |
| Mg | 100 |
| CRP | 100 |
| ChE | 100 |
| LD | 100 |
| γ-GTP | 100 |
| T-BIL | 100 |
| D-BIL | 100 |
| AMY | 100 |
| ALB | 100 |
| IgA | 100 |
| IgG | 100 |
| IgM | 100 |

When the user operates the automatic analyzer on the basis of, for example, Operation Set 1 used for periodic medical examinations shown in Table 1, the number of required analysis items is limited, for Operation Set 1 is used for periodic medical examinations. However, the number of analysis samples registered for each analysis item is large. In contrast, in Operation Set 2 for nighttime shown in Table 1, many analysis items need to be analyzed due to various night-time analysis requests. However, the number of samples to be analyzed is not larger than those in regular medical examinations, and the number of analysis samples to be registered is thus smaller. When analysis items and the number of analysis samples are registered as an operation set proper for each automatic analyzer operation as above, various operation modes can be supported.

A method for changing the operation mode of the automatic analyzer using an operation set will be described in accordance with the process flowchart shown in FIG. 2. In Step 201 shown in FIG. 2, an operation set is registered for each operation mode. Each of the operation sets constitutes a combination of analysis items and analysis sample numbers for the analysis items. In Step 202 shown in FIG. 2, an operation set is selected. Reagents required for the selected operation set are then checked to identify analysis items that can be analyzed by all the reagents placed in the first reagent storing unit 33 and in the second reagent storing unit 100 and to calculate the number of tests for each of the identified analysis items. Next, in Step 207 of FIG. 2, the operation set is changed. In Step 208 of FIG. 2, reagents are replaced between the first reagent storing unit 33 and the second reagent storing unit 100. In Step 212 of FIG. 2, relevant reagents are placed in the first reagent storing unit 33; the reagents are in agreement with the analysis items and the number of planned analyses for each of the analysis items in the operation set.

Hereinafter, means for selecting reagents used for the analysis operation based on an operation set is referred to as "reagent selection means," in which operation set analysis items each combined with the scheduled number of analyses are registered.

Next, steps executed by the reagent selection means will be sequentially described in detail.

Registration of an operation set, which corresponds to Step 201 of FIG. 2, will be described with reference to FIG. 3. An operation set name is registered in an operation set list 401. Next, an analysis item is selected from an analysis item list 402, and the selected analysis item is then added by use of an "Add" button 403. Unnecessary items can be selected from among analysis items registered in an operation-set item list 404 and deleted by use of a "Delete" button 405. Radio buttons 406 for selecting a method for setting the number of tests can be used to select the manual setting mode or the automatic setting mode. In the manual setting mode, the user manually sets the number of analyses for each analysis item. After that, the settings which have been set by use of the "Add" button 403 and the "Delete" button 405 are fixed by use of an "Update" button 407. Lastly, the above settings are registered by use of a "Register" button 408. The above settings can be cancelled by use of a "Cancel" button 409.

Here, data relating to the operation set includes analysis item names; the number of tests; reagent names; data (bar code) used to identify reagent cassettes; the validity dates of reagents; and analysis logs. These are written onto recording media built into the overall control computer 11 or the control computers 12, 13, 14, and 15. This makes it possible to easily set/register an operation set and to easily control transfer of reagents.

As Step 202 of FIG. 2, how to select an operation set will be described with reference to FIG. 4.

Figure 3:
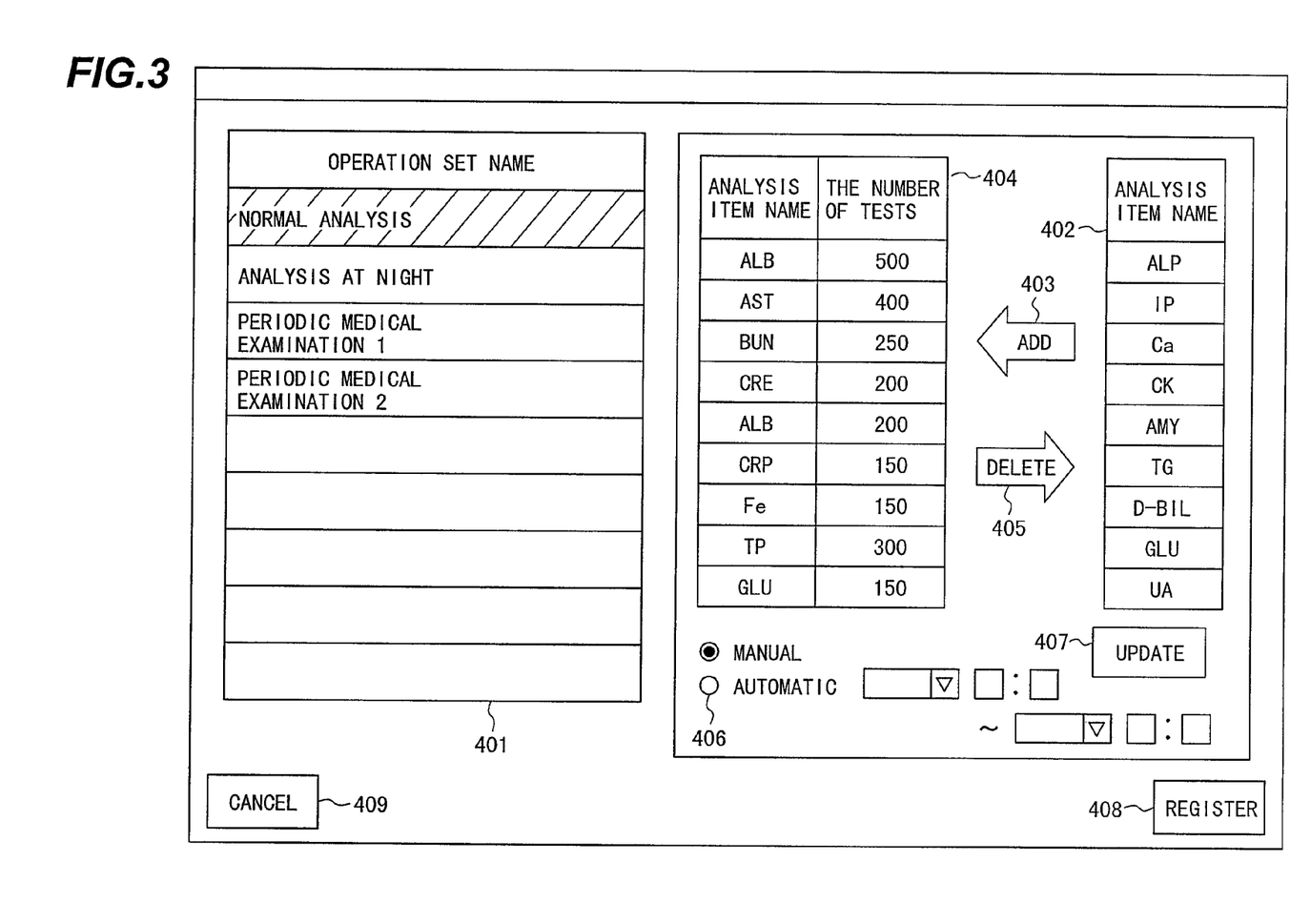
FIG. 3 is a diagram illustrating an operation-set registration screen according to one embodiment of the present invention.

An operation mode required at a certain point of time is selected from all registered operation sets shown in FIG. 3 (this embodiment shows a case where "normal analysis" is selected by use of an operation-set selection combo box 501). A "Check placed reagents" button 502 is then clicked to identify analysis items that can be analyzed by all reagents placed in the first reagent storing unit 33 and in the second reagent storing unit 100, and to calculate the number of tests corresponding to each of the analysis items that can be analyzed.

Figure 2:
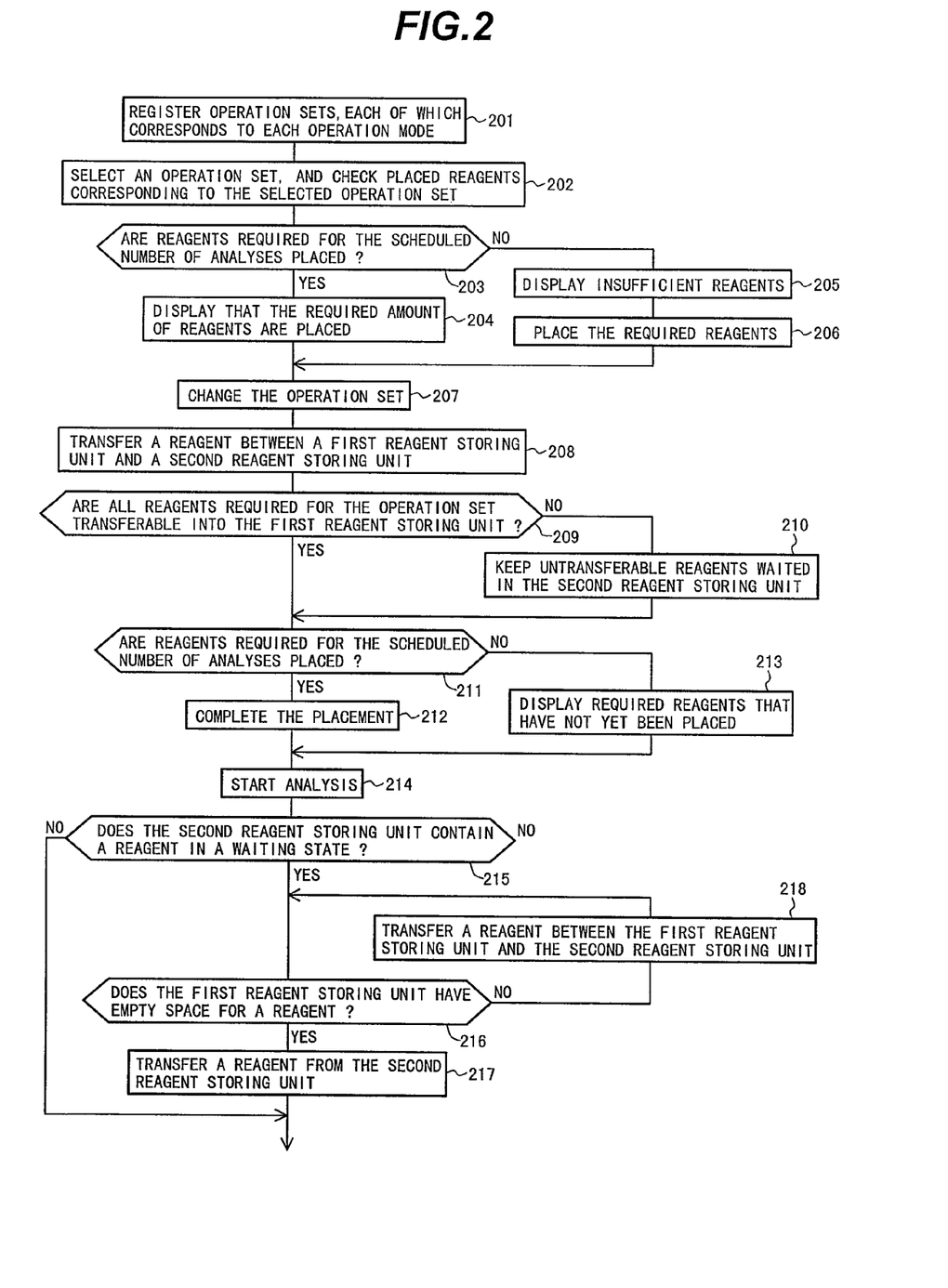
FIG. 2 is a process flowchart illustrating steps ranging from the registration of an operation set to an analysis according to one embodiment of the present invention.
Figure 4:
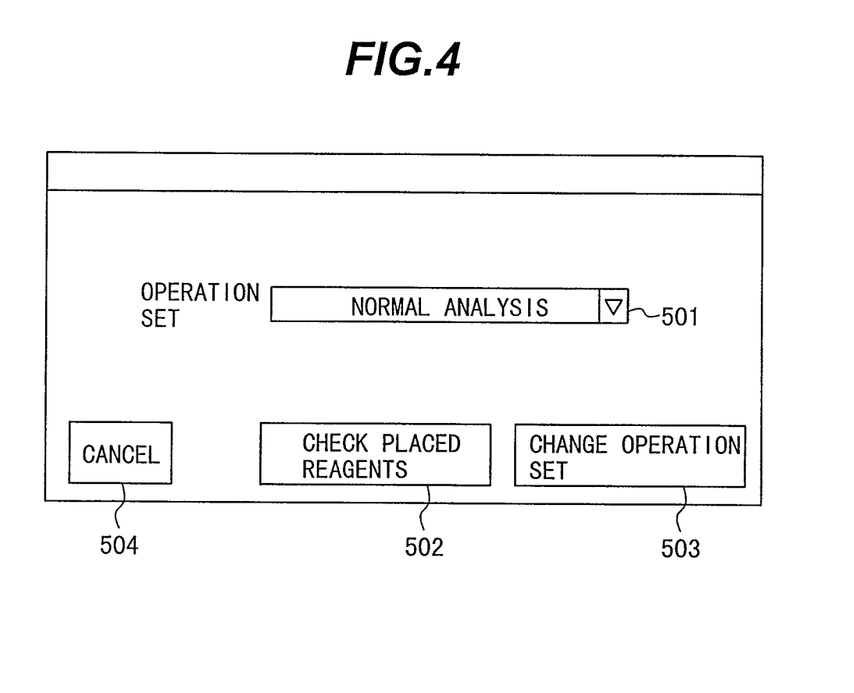
FIG. 4 is a diagram illustrating an operation-set changing screen according to one embodiment of the present invention.
Figure 5:
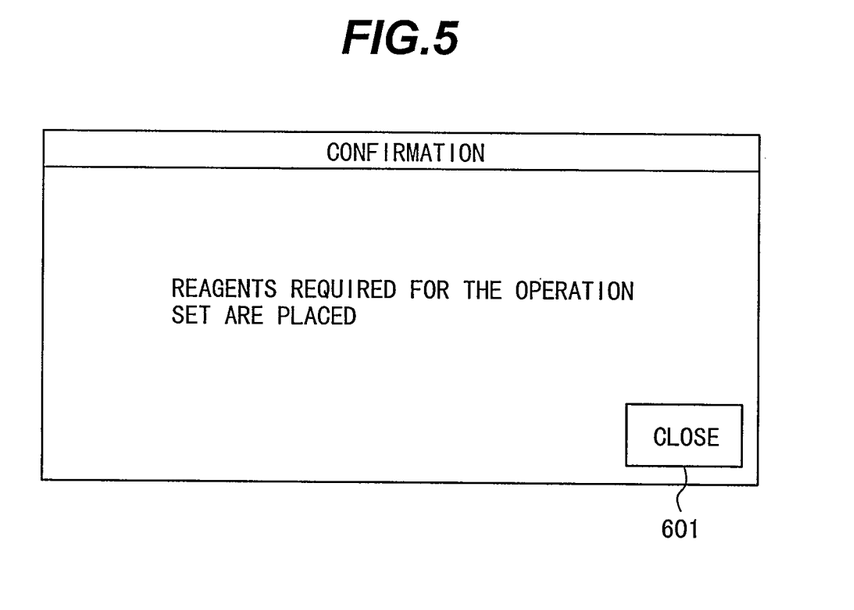
FIG. 5 is a diagram illustrating a confirmation screen presented when reagents which enable analyses based on an operation set are placed according to one embodiment of the present invention.
Figure 6:
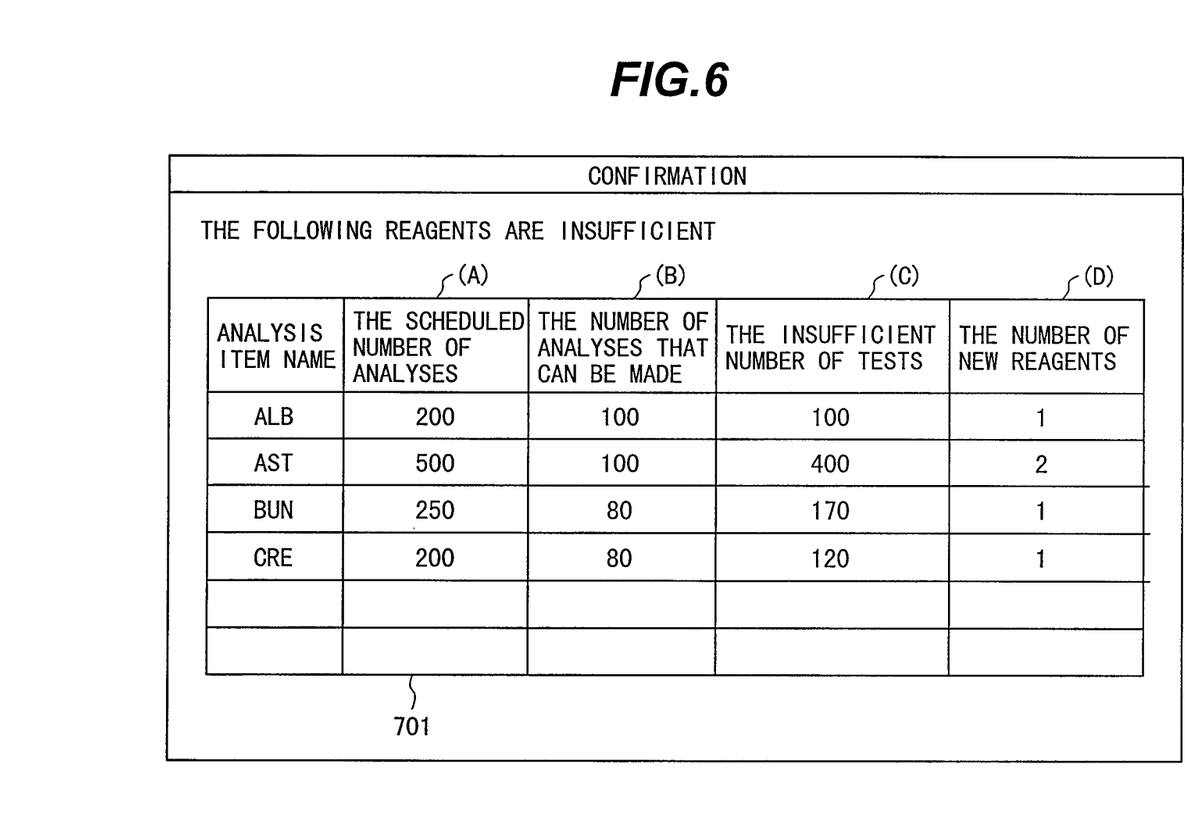
FIG. 6 is a diagram illustrating a screen for displaying a list of reagents insufficient for an operation set according to one embodiment of the present invention.

In Step 203 shown in FIG. 2, the identified analysis items that can be analyzed by use of all reagents placed in the first reagent storing unit 33 and in the second reagent storing unit 100, and the calculated number of tests corresponding to each of the analysis items that can be analyzed, both of which have been obtained according to Step 202 shown in FIG. 2, are compared with the analysis items of the operation set selected in FIG. 4 and the scheduled number of analyses corresponding to each of the analysis items respectively. If it is judged that reagents required for the analysis operation based on the operation set are placed, a confirmation screen as shown in FIG. 5 is displayed in Step 204 shown in FIG. 2. Clicking a "Close" button 601 completes the confirmation. However, as a result of the placed reagent check in Step 203 shown in FIG. 2, if it is judged that the reagents required for the analysis operation based on the operation set are not placed, insufficient reagents are displayed as shown in FIG. 6. This corresponds to Step 205 shown in FIG. 2. In the example shown in FIG. 6, for the analysis items specified in the selected operation set, and for the scheduled number of analyses corresponding to each of the analysis items, information is displayed in a reagent information list 701. The displayed information includes: a name of an analysis item for which a reagent is insufficient; the scheduled number of analyses (A) specified in the operation set; the number of analyses (B) that can be made by use of currently placed reagents; and the insufficient number of tests (C). Additionally, the number of new reagents (D) is displayed. This is the number of additional reagents required to satisfy the scheduled number of analyses specified in the operation set when the user is required to add new reagents. The number of new reagents (D) enables the user to know the number of reagents that should be placed. Here, as Step 206 shown in FIG. 2, the user places the reagents in the second reagent storing unit 100. In this case, Step 206 shown in FIG. 2 may also be omitted. More specifically, the user is allowed not to place reagents if necessary although the user knows that the reagents are insufficient.

In Step 207 shown in FIG. 2, in order to place, in the first reagent storing unit 33, reagents required for the scheduled number of tests specified in the operation set, a "Change operation set" button 503 shown in FIG. 4 is clicked. As a result, in Step 208, a reagent is transferred between the first reagent storing unit and the second reagent storing unit. In this case, an insufficient reagent is transferred from the second reagent storing unit 100 to the first reagent storing unit 33 so as to enable analyses, the number of which is equivalent to the scheduled number of analyses corresponding to each analysis item registered in the specified operation set. If the first reagent storing unit 33 does not have empty space for a reagent to be placed therein, with the result that no reagent can be transferred to the first reagent storing unit 33, a reagent, which is not required for analysis items specified in the operation set, and which is not required for the scheduled number of analyses corresponding to each of the analysis items, is transferred from the first reagent storing unit 33 to the second reagent storing unit 100. As a result, the first reagent storing unit 33 is provided with empty space for a required reagent to be placed therein. Until all reagents, which are required for the analysis items specified in the operation set, and which are required for the scheduled number of analyses corresponding to each of the analysis items, are placed in the first reagent storing unit 33, reagents are transferred between the first reagent storing unit 33 and the second reagent storing unit 100.

Hereinafter, means for, when the first reagent storing unit does not have empty space for a reagent to be placed therein, with the result that all reagents required for analysis operation based on the operation set cannot be completely transferred to the first reagent storing unit, keeping the required reagent waiting in the second reagent storing unit, and for, when the first reagent storing unit is provided with empty space for a reagent to be placed therein, making a judgment as to whether or not to transfer the reagent to the first reagent storing unit, is referred to as "transferability judgment means".

Incidentally, when a "Cancel" button 504 shown in FIG. 4 is clicked, the process proceeds to a next step without checking placed reagents, and without changing the operation set.

In the case of an operation set in which the scheduled number of analyses corresponding to each analysis item is large, a large number of analysis items may require that a plurality of reagents be placed in the first reagent storing unit 33 on an analysis item basis. In this case, however, in Step 209 shown in FIG. 2, such a situation can also be thought to occur that all reagent, which are required for analysis items specified in the operation set, and which are required for the scheduled number of analyses corresponding to each of the analysis items, cannot be completely transferred to the first reagent storing unit 33. In such a case, as Step 210 shown in FIG. 2, when reagents which could not be transferred to the first reagent storing unit 33 are kept waiting in the second reagent storing unit 100; the reagents are kept waiting in the second reagent storing unit 100 with a higher priority placed on a reagent, the required number of which is two or more for an identical item, and in decreasing order of the scheduled number of analyses specified in the operation set. This enables the first reagent storing unit 33 to always contain at least one reagent required for each of the analysis items specified in the operation set.

Figure 7:
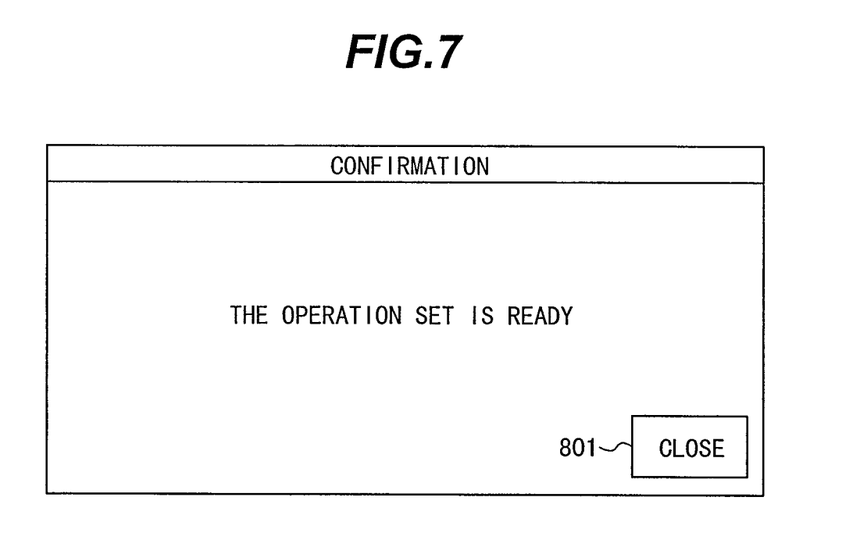
FIG. 7 is a diagram illustrating a confirmation screen presented when transfer of a reagent required for an operation set is completed according to one embodiment of the present invention.

On the completion of the reagent transfer operation, in Step 211 shown in FIG. 2, a judgment is made again as to whether or not the reagents required for the operation set are placed in the first reagent storing unit 33 and in the second reagent storing unit 100. The user's attention is then attracted. Here, if it is judged that the reagents required for the operation set are placed, the placement has been completed in Step 212 shown in FIG. 2, and a confirmation screen as shown in FIG. 7 is displayed. Clicking a "Close" button 801 completes the confirmation. However, if it is not judged that the reagents required for the operation set are placed in the first reagent storing unit 33 and in the second reagent storing unit 100 (for example, there is a case where although insufficient reagents are displayed in Step 205 shown in FIG. 2, the reagents have not yet been placed in Step 206 shown in FIG. 2; or there is a case where although the reagents have been placed in Step 206 shown in FIG. 2, the reagents are insufficient for the scheduled number of analyses), then, in Step 213, information is displayed again in the reagent information list 701 as shown in FIG. 6. The displayed information includes: a name of an analysis item for which a reagent is insufficient; the scheduled number of analyses (A) specified in the operation set; the number of analyses (B) that can be made by currently placed reagents; the number of insufficient tests (C); and the number of new reagents (D) required when new reagents are placed.

When analysis is started in Step 214 shown in FIG. 2, a reagent which cannot be used for the analysis may occur for some reasons (for example, the validity time is expired) In Step 215 shown in FIG. 2, a judgment is made as to whether or not the second reagent storing unit 100 contains a reagent to be transferred to the first reagent storing unit 33. If it is judged that the second reagent storing unit 100 contains a reagent to be transferred to the first reagent storing unit 33, a judgment is made in Step 216 in FIG. 2 as to whether or not the first reagent storing unit 33 has empty space for a reagent to be placed therein, or whether or not the first reagent storing unit 33 has an area in which a reagent which cannot be used for the analysis is placed.

If it is judged to be "Yes" in Step 216, a reagent kept waiting in the second reagent storing unit 100 is transferred to the empty space or the area in question in Step 217 shown in FIG. 2. In contrast, if it is judged that the first reagent storing unit 33 has empty space for a reagent to be placed therein, or it is judged that the first reagent storing unit 33 has an area in which a reagent which cannot be used for the analysis is placed, then in Step 218, a reagent required for the analysis is transferred to the first reagent storing unit by replacing the reagent which cannot be used for the analysis or a reagent excessively stored in the first reagent storing unit with the reagent kept waiting in the second reagent storing unit 100. As described above, each reagent kept waiting in the second reagent storing unit 100 is transferred to the first reagent storing unit 33 every time the first reagent storing unit 33 is provided with empty space for a reagent to be placed therein.

As a result, even in the case of an operation set in which the scheduled number of analyses corresponding to each analysis item is large (for example, an operation set used for multi-sample analysis), analyses can be continued by use of reagents prepared before the start of the analyses.

In Step 201 shown in FIG. 2, when the scheduled number of analyses to be specified in the operation set is determined, if "Automatic" is selected, the user is prompted to specify the day of the week and the time at which analysis will be started, and the day of the week and the time at which the analysis will be ended. Accordingly, the scheduled number of analyses corresponding to each analysis item, which are to be made within the specified period of time, is automatically determined on the basis of the number of analyses corresponding to each analysis item recorded as past analysis recording. The number of analyses corresponding to each analysis item within a specified past period of time can be calculated by recording the number of analyses as the analysis recording with the number of analyses linked with information including the measurement date and time of each analysis item, and the kind of examination.

Hereinafter, the means for automatically determining the scheduled number of analyses corresponding to each analysis item defined in the operation set on the basis of the number of analyses corresponding to each analysis item recorded as the past analysis recording is referred to as "scheduled-number-of-analyses automatic determination means".

As an example of a method for automatically determining the scheduled number of analyses, for example, if a period of time is specified at the time of registering an operation set, the average number of analyses corresponding to each analysis item, which have been made within the same time range in the past corresponding to the specified period of time, is automatically determined as the scheduled number of analyses for the specified period of time. The above method will be described with reference to Table 2. When a period of time during which analyses are made, and an analysis item, are specified (in Table 2, a time range from Monday 9:00 to Monday 17:00 is specified as the period of time; and AST is specified as the analysis item), analysis recording covering analyses of the specified analysis item made during the specified period of time is extracted from the past analysis recording to calculate the number of analyses for the specified period of time (Table 2 shows the number of analyses measured within the specified period of time on a week basis). Therefore, the average number of analyses measured within the same time range in the past is determined as the scheduled number of analyses for the specified period of time.

TABLE 2

An example of the calculation of the scheduled number of analyses
Specified time range: Monday 9:00 to Monday 17:00
Analysis item name: AST

| Time range | The number of analyses |
|---|---|
| The first Monday of April, 2007 | 150 tests |
| The second Monday of April, 2007 | 135 tests |
| The third Monday of April, 2007 | 160 tests |
| The fourth Monday of April, 2007 | 170 tests |

The average number of analyses: 154 test
The maximum number of analyses: 170 test As another example of the method for automatically determining the scheduled number of analyses, for example, if a period of time is specified at the time of registering an operation set, the maximum number of analyses which have been made within the same time range in the past is automatically determined as the scheduled number of analyses for the specified period of time. In this case, even if requests for analysis accidentally increases, it is possible to minimize the possibility that insufficient reagent will occur.

In the above-described embodiments, the above processes can be automatically executed by recording a program for instructing a computer to function as the above means, or a program for instructing the computer to execute the above processes, in a computer-readable storage medium that is built into the overall control computer 11 or the control computers 12, 13, 14, and 15.

What is claimed is:

1. A method for using an automatic analyzer, said automatic analyzer including:
    a reaction unit including a plurality of vessels;
    a first reagent storing unit that is capable of storing a plurality of reagent cassettes;
    a sample dispenser for dispensing a sample into the reaction unit;
    a reagent dispenser for dispensing a reagent corresponding to an analysis item from the first reagent storing unit into the reaction unit;
    a second reagent storing unit that is capable of storing a plurality of reagent cassettes; and
    reagent cassette transfer means for transferring a reagent cassette containing a reagent between the first reagent storing unit and the second reagent storing unit;
    said method comprising the sequence of steps of:
    registering a plurality of operation sets, where the operation sets each specify one or more combinations of analysis items and a scheduled number of analyses corresponding to the analysis items;
    selecting an operation set from the registered operation sets;
    determining a scheduled number of analyses of the analysis items defined in the operation set based on a number of analyses of the analysis items recorded in a past analysis record;
    replacing, prior to the start of analysis according to the selected operation set, the reagents such that the reagent cassettes stored in the first reagent storing unit contain reagents sufficient to support the combination of analysis items and scheduled number of analyses of the selected operation set by controlling carrying in of reagent cassettes by the reagent cassette transfer means from the second reagent storing unit to the first reagent storing unit and taking out of the reagent cassettes by the reagent cassette transfer means from the first reagent storing unit to the second reagent storing unit;
    when the first reagent storing unit does not have empty space for a reagent to be placed therein, with the result that all reagents required for analysis operation based on the selected operation set cannot be completely transferred to the first reagent storing unit, keeping the required reagent waiting in the second reagent storing unit; and
    when the first reagent storing unit is provided with empty space for a reagent to be placed therein, transferring the required reagent to the first reagent storing unit.

2. The method for using the automatic analyzer according to claim 1, said method further comprising the step of:
    selecting one operation set from among the registered operation sets, the number of which is at least one.

3. The method for using the automatic analyzer according to claim 1, said method further comprising the step of:
    displaying a reagent corresponding to the analysis item when the reagent is required for an analysis item specified by the operation set and is not placed in the first reagent storing unit or the second reagent storing unit.

4. The method for using the automatic analyzer according to claim 1, said method further comprising the step of:
    automatically determining the scheduled number of analyses corresponding to each analysis item defined in the operation set on the basis of the number of analyses corresponding to each analysis item recorded as past analysis recording.

5. The method for using the automatic analyzer according to claim 1, said method further comprising the step of:
    selecting between a case where the scheduled number of analyses of individual analysis items defined in the operation set is manually specified, and a case where the scheduled number of analyses of individual analysis items defined in the operation set are automatically determined on the basis of the number of analyses of individual analysis items recorded as the past analysis recording.

* * * * *